(12) United States Patent
Kossmann et al.

(10) Patent No.: US 6,617,495 B2
(45) Date of Patent: Sep. 9, 2003

(54) NUCLEIC ACID MOLECULES FROM PLANTS CODING ENZYMES WHICH PARTICIPATE IN THE STARCH SYNTHESIS

(75) Inventors: Jens Kossmann, Golm (DE); Claus Frohberg, Berlin (DE)

(73) Assignee: PlantTec Biotechnologie GmbH (DE)

( * ) Notice: Subject to any disclaimer, the term of this patent is extended or adjusted under 35 U.S.C. 154(b) by 0 days.

(21) Appl. No.: 09/780,115

(22) Filed: Feb. 9, 2001

(65) Prior Publication Data

US 2001/0011378 A1 Aug. 2, 2001

Related U.S. Application Data

(62) Division of application No. 09/115,704, filed on Jul. 15, 1998, now Pat. No. 6,211,436, which is a continuation of application No. PCT/EP97/00158, filed on Jan. 15, 1997.

(30) Foreign Application Priority Data

Jan. 16, 1996 (DE) .......................... 196 01 365

(51) Int. Cl.$^7$ .................. C12N 15/29; C12N 15/82; C12N 5/04; A01H 5/00; C12P 19/04
(52) U.S. Cl. .................. 800/284; 800/278; 800/320; 800/320.1; 800/320.2; 800/320.3; 800/317.2; 800/286; 435/320.1; 435/419; 536/23.6; 536/24.5
(58) Field of Search ............... 536/23.6, 24.5; 435/320.1, 419; 800/278, 284, 320, 320.1, 320.2, 320.3, 317.2, 286

(56) References Cited

U.S. PATENT DOCUMENTS 5,824,790 A 10/1998 Keeling et al. ............ 536/23.6

FOREIGN PATENT DOCUMENTS

| AU | 713978 | 6/1996 |
|---|---|---|
| AU | 74268/96 | 7/1997 |
| CA | 2061443 | 8/1993 |
| JP | 60-70779 | 3/1994 |
| WO | WO 92/11376 | 7/1992 |
| WO | WO 94/09144 | 4/1994 |
| WO | WO 94/11520 | 5/1994 |
| WO | WO 97/10328 | 3/1997 |
| WO | WO 97/20936 | 6/1997 |

OTHER PUBLICATIONS

Abel, G.J.W., "Untersuchungen zur Funktion von Stärke–Synthasen in der Kartoffel (*Solanum tuberosum* L.)", PhD Thesis, Freie Universität Berlin, Germany (defended on Nov. 3, 1995).

T. Baba et al., "Identification, cDNA Cloning, and Gene Expression of Soluble Starch Synthesis in Rick (*Oryza sativa* L.) Immature Seeds", *Plant Physiol*, 103, pp. 565–573 (1993).

A. Edwards et al., "Biochemical and Molecular Characterization of a Novel Starch Synthase from Potato Tubers," *The Plant Journal*, 8(2), pp. 283–294 (1995).

R.B. Klösgen et al., "Molecular Analysis of the waxy Locus of *Zea mays*," Molec. Gen. Genet., 203, pp. 237–244 (1986).

Kossmann et al., "Transgenic Plants as a Tool to Understand Starch Biosynthesis," Progress in Biotechnol., 10, pp. 271–278 (1995).

C. Mu et al., "Association of a 76 kDa Polypeptide with Soluble Starch Synthase 1 Activity in Maize (cvB73) Endosperm," The Plant Journal, 6(2), pp. 151–159 (1994).

B. Müller–Röber et al., "Approaches to Influence Starch Quantity and Starch Quality in Transgenic Plants," *Plant, Cell and Environment*, 17, pp. 601–613 (1994).

R.G.F. Visser et al., "Inhibition of the Expression of the Gene for Granule–bound Starch Synthase in Potato by Antisense Constructs," Molec. Gen. Genet., 225, pp. 289–296 (1991).

*Primary Examiner*—David T. Fox
(74) *Attorney, Agent, or Firm*—Fish & Neave; James F. Haley, Jr.; Grant Kalinowski

(57) ABSTRACT

Nucleic acid molecules encoding enzymes which participate in the starch synthesis in plants are described. These enzymes are a novel isotype of starch synthase.

Furthermore, the invention relates to vectors and hose cells which were transformed with the described nucleic acid molecules, in particular to transformed plant cells and to plants which may be regenerated therefrom and which exhibit an increased or reduced activity of the described proteins.

14 Claims, No Drawings

SEQUENCE LISTING

<160> NUMBER OF SEQ ID NOS: 2

<210> SEQ ID NO 1
<211> LENGTH: 2652
<212> TYPE: DNA
<213> ORGANISM: Zea mays
<220> FEATURE:
<221> NAME/KEY: CDS
<222> LOCATION: (9)..(2213)

<400> SEQUENCE: 1

```
gaattcgg cac gag aat ttt cta aaa gga aag ctt att gag ata act gag      50
         His Glu Asn Phe Leu Lys Gly Lys Leu Ile Glu Ile Thr Glu
          1               5                   10 aca gag gag agt cta ttc aag ttg gag aaa gag tgt gct ctt cta aat      98
```

```
                                                       -continued

Thr Glu Glu Ser Leu Phe Lys Leu Glu Lys Glu Cys Ala Leu Leu Asn
 15                  20                  25                  30 gct tcc ctt agg gag ctc gag tgt aca tcc act tct gcc caa tct gat    146
Ala Ser Leu Arg Glu Leu Glu Cys Thr Ser Thr Ser Ala Gln Ser Asp
                 35                  40                  45 gtg ttg aaa ctt ggc cct ctg caa caa gat gcc tgg tgg gag aaa gta    194
Val Leu Lys Leu Gly Pro Leu Gln Gln Asp Ala Trp Trp Glu Lys Val
             50                  55                  60 gaa aat ttg gaa gac ttg ctt gat tcc aca gca aac caa gtg gag cat    242
Glu Asn Leu Glu Asp Leu Leu Asp Ser Thr Ala Asn Gln Val Glu His
         65                  70                  75 gct tct ttg acg cta gat ggt tac cgt gat ttc cag gat aag gtt gac    290
Ala Ser Leu Thr Leu Asp Gly Tyr Arg Asp Phe Gln Asp Lys Val Asp
     80                  85                  90 aaa cta aaa gca tca ttg gga aca aca aac gta tca gag ttc tgt ctt    338
Lys Leu Lys Ala Ser Leu Gly Thr Thr Asn Val Ser Glu Phe Cys Leu
 95                 100                 105                 110 tat ttg gtt gat att ttg cag caa agg gta aaa tca gta gaa gag cgc    386
Tyr Leu Val Asp Ile Leu Gln Gln Arg Val Lys Ser Val Glu Glu Arg
                 115                 120                 125 ttt caa gca tgt aat cat gaa atg cat tca caa att gaa ctt tat gaa    434
Phe Gln Ala Cys Asn His Glu Met His Ser Gln Ile Glu Leu Tyr Glu
             130                 135                 140 cac tca ata gtg gag ttt cat ggt act ctc agc aaa cta ata aat gaa    482
His Ser Ile Val Glu Phe His Gly Thr Leu Ser Lys Leu Ile Asn Glu
         145                 150                 155 agt gag aaa aag tca atg gag cat tat gca gaa ggc atg cca tca gag    530
Ser Glu Lys Lys Ser Met Glu His Tyr Ala Glu Gly Met Pro Ser Glu
     160                 165                 170 ttc tgg agt agg atc tct ctt ctg att gat ggg tgg tcg ctt gag aag    578
Phe Trp Ser Arg Ile Ser Leu Leu Ile Asp Gly Trp Ser Leu Glu Lys
175                 180                 185                 190 aaa ata tcc att aat gat gca agt atg ttg aga gaa atg gct tgg aaa    626
Lys Ile Ser Ile Asn Asp Ala Ser Met Leu Arg Glu Met Ala Trp Lys
                 195                 200                 205 agg gat aat cgc ctc cgg gaa gct tac ttg tca tcc aga gga atg gaa    674
Arg Asp Asn Arg Leu Arg Glu Ala Tyr Leu Ser Ser Arg Gly Met Glu
             210                 215                 220 gag agg gaa ctg ata gat agt ttt cta aag atg gca cta cca gga aca    722
Glu Arg Glu Leu Ile Asp Ser Phe Leu Lys Met Ala Leu Pro Gly Thr
         225                 230                 235 agt tct ggt ttg cac att gtc cac ata gca gca gag atg gct cct gtc    770
Ser Ser Gly Leu His Ile Val His Ile Ala Ala Glu Met Ala Pro Val
     240                 245                 250 gca aag gtt ggt ggt ctg gca gat gtg atc tct ggt ctt ggg aag gca    818
Ala Lys Val Gly Gly Leu Ala Asp Val Ile Ser Gly Leu Gly Lys Ala
255                 260                 265                 270 ctt caa aaa aag ggg cac ctt gta gag att att ctt ccc aaa tat gat    866
Leu Gln Lys Lys Gly His Leu Val Glu Ile Ile Leu Pro Lys Tyr Asp
                 275                 280                 285 tgc atg cag cat aac caa ata aat aat ctt aag gtt cta gat gtt gtg    914
Cys Met Gln His Asn Gln Ile Asn Asn Leu Lys Val Leu Asp Val Val
             290                 295                 300 gtg aag tct tac ttt gaa gga aat atg ttt gcc aac aag ata tgg act    962
Val Lys Ser Tyr Phe Glu Gly Asn Met Phe Ala Asn Lys Ile Trp Thr
         305                 310                 315 gga act gtt gaa ggt ctt ccg gtc tac ttt att gaa ccg caa cat cca   1010
Gly Thr Val Glu Gly Leu Pro Val Tyr Phe Ile Glu Pro Gln His Pro
     320                 325                 330
```

-continued

```
ggt aag ttc ttc tgg agg gca caa tac tac gga gag cat gat gac ttc    1058
Gly Lys Phe Phe Trp Arg Ala Gln Tyr Tyr Gly Glu His Asp Asp Phe
335             340             345             350 aaa cgt ttt tcg tac ttt agc cgt gtt gca ctg gaa ttg ctt tac caa    1106
Lys Arg Phe Ser Tyr Phe Ser Arg Val Ala Leu Glu Leu Leu Tyr Gln
            355             360             365 tct ggg aag aaa gtt gac ata att cac tgc cat gac tgg cag act gca    1154
Ser Gly Lys Lys Val Asp Ile Ile His Cys His Asp Trp Gln Thr Ala
        370             375             380 ttt gtt gca cct ctt tac tgg gat gta tat gca aac ctg ggc ttc aac    1202
Phe Val Ala Pro Leu Tyr Trp Asp Val Tyr Ala Asn Leu Gly Phe Asn
    385             390             395 tca gct aga att tgt ttt acc tgt cac aat ttt gaa tat caa gga atc    1250
Ser Ala Arg Ile Cys Phe Thr Cys His Asn Phe Glu Tyr Gln Gly Ile
400             405             410 gct cca gct cag gac tta gca tat tgt ggt ctt gat gtt gat cac ctg    1298
Ala Pro Ala Gln Asp Leu Ala Tyr Cys Gly Leu Asp Val Asp His Leu
415             420             425             430 gat aga cca gac aga atg cgg gat aat tca cat ggc aga ata aat gtt    1346
Asp Arg Pro Asp Arg Met Arg Asp Asn Ser His Gly Arg Ile Asn Val
            435             440             445 gtt aag ggt gca gtt gta tat tcc aac att gtg aca act gta tca cca    1394
Val Lys Gly Ala Val Val Tyr Ser Asn Ile Val Thr Thr Val Ser Pro
        450             455             460 aca tat gca caa gag gtt cgc tca gag ggt ggg cgt ggg ctc caa gat    1442
Thr Tyr Ala Gln Glu Val Arg Ser Glu Gly Gly Arg Gly Leu Gln Asp
    465             470             475 aca ctc aaa gtg cac tcc aag aaa ttt gtt gga ata ctt aat ggc att    1490
Thr Leu Lys Val His Ser Lys Lys Phe Val Gly Ile Leu Asn Gly Ile
480             485             490 gac aca gat act tgg aat ccg tct acg gat agg ttt ctc aag gtt caa    1538
Asp Thr Asp Thr Trp Asn Pro Ser Thr Asp Arg Phe Leu Lys Val Gln
495             500             505             510 tac agt gct aat gat cta tat gga aag tca gca aac aaa gca gct ctt    1586
Tyr Ser Ala Asn Asp Leu Tyr Gly Lys Ser Ala Asn Lys Ala Ala Leu
            515             520             525 agg aag cag ttg aag ctt gct tcc aca caa gct tct caa cca tta gtt    1634
Arg Lys Gln Leu Lys Leu Ala Ser Thr Gln Ala Ser Gln Pro Leu Val
        530             535             540 ggt tgc att acg agg cta gtt cct caa aag ggt gta cat ctc atc agg    1682
Gly Cys Ile Thr Arg Leu Val Pro Gln Lys Gly Val His Leu Ile Arg
    545             550             555 cat gca ata tat aaa ata act gag ttg ggt ggt caa ttt gtt ctg ctg    1730
His Ala Ile Tyr Lys Ile Thr Glu Leu Gly Gly Gln Phe Val Leu Leu
560             565             570 ggt tca agt cca gta cag cat atc cag aga gag ttc gag ggt att gcg    1778
Gly Ser Ser Pro Val Gln His Ile Gln Arg Glu Phe Glu Gly Ile Ala
575             580             585             590 gac caa ttt cag aac aac aac aat gtc agg ctg ctt ttg aag tat gat    1826
Asp Gln Phe Gln Asn Asn Asn Asn Val Arg Leu Leu Leu Lys Tyr Asp
            595             600             605 gat gct ctg gca cat atg atc ttt gca gca tca gac atg ttc att gtt    1874
Asp Ala Leu Ala His Met Ile Phe Ala Ala Ser Asp Met Phe Ile Val
        610             615             620 cct tct atg ttt gaa cca tgt ggc ctc act cag atg gta gct atg cga    1922
Pro Ser Met Phe Glu Pro Cys Gly Leu Thr Gln Met Val Ala Met Arg
    625             630             635 tat ggt tct gtg cca gtt gtt cgg aga acc ggc ggt ttg aat gac agt    1970
Tyr Gly Ser Val Pro Val Val Arg Arg Thr Gly Gly Leu Asn Asp Ser
640             645             650
```

-continued

```
gtc ttc gat ttg gac gat gaa acg ata ccc atg gag gtg cga aat ggc    2018
Val Phe Asp Leu Asp Asp Glu Thr Ile Pro Met Glu Val Arg Asn Gly
655                 660                 665                 670 ttc acc ttt ttg aag gct gat gag cag gat ttt ggt aat gca ctg gaa    2066
Phe Thr Phe Leu Lys Ala Asp Glu Gln Asp Phe Gly Asn Ala Leu Glu
                675                 680                 685 aga gct ttc aac tac tac cac aga aaa cct gaa gtt tgg aaa cag ttg    2114
Arg Ala Phe Asn Tyr Tyr His Arg Lys Pro Glu Val Trp Lys Gln Leu
            690                 695                 700 gtg cag aaa gac atg aag ata gat ttc agc tgg gat act tca gtt tct    2162
Val Gln Lys Asp Met Lys Ile Asp Phe Ser Trp Asp Thr Ser Val Ser
        705                 710                 715 caa tac gaa gaa atc tat cag aaa aca gcc act cga gcc agg gca gcg    2210
Gln Tyr Glu Glu Ile Tyr Gln Lys Thr Ala Thr Arg Ala Arg Ala Ala
    720                 725                 730 gca taaacagcag agacattgag acagttccct gctgtctcca tgaagtctcc        2263
Ala
735 tagatgctgt gcttaaccgt atggtaaaga aatatggtct gtatcagctc agaattaagc 2323
atctgccgag gaagcgcggt gcatccggac tcgggtgtac aaggggcgac gtggcgttac 2383
gtgcagtccc caacgaagca aagagacaga agtacagctg tacagaacgg atatcttgtg 2443
aagcacacat tgggatcagg acgtttggtg ctgcagctac tttcggtgca aagcacata  2503
tatacgagac ctgccagggc gagcaaatac ccagttatac acgcgattgc tcagctctat 2563
caagctgtga attgaaagat ttctatagtg tattcacgcg acgttttcat aaactagtgt 2623
gagttatgta ctctgaccaa aaaaaaaa                                    2652

<210> SEQ ID NO 2
<211> LENGTH: 735
<212> TYPE: PRT
<213> ORGANISM: Zea mays

<400> SEQUENCE: 2

His Glu Asn Phe Leu Lys Gly Lys Leu Ile Glu Ile Thr Glu Thr Glu
  1               5                  10                  15

Glu Ser Leu Phe Lys Leu Glu Lys Glu Cys Ala Leu Leu Asn Ala Ser
             20                  25                  30

Leu Arg Glu Leu Glu Cys Thr Ser Thr Ser Ala Gln Ser Asp Val Leu
         35                  40                  45

Lys Leu Gly Pro Leu Gln Gln Asp Ala Trp Trp Glu Lys Val Glu Asn
     50                  55                  60

Leu Glu Asp Leu Leu Asp Ser Thr Ala Asn Gln Val Glu His Ala Ser
 65                  70                  75                  80

Leu Thr Leu Asp Gly Tyr Arg Asp Phe Gln Asp Lys Val Asp Lys Leu
                 85                  90                  95

Lys Ala Ser Leu Gly Thr Thr Asn Val Ser Glu Phe Cys Leu Tyr Leu
            100                 105                 110

Val Asp Ile Leu Gln Gln Arg Val Lys Ser Val Glu Glu Arg Phe Gln
        115                 120                 125

Ala Cys Asn His Glu Met His Ser Gln Ile Glu Leu Tyr Glu His Ser
    130                 135                 140

Ile Val Glu Phe His Gly Thr Leu Ser Lys Leu Ile Asn Glu Ser Glu
145                 150                 155                 160

Lys Lys Ser Met Glu His Tyr Ala Glu Gly Met Pro Ser Glu Phe Trp
                165                 170                 175
```

```
Ser Arg Ile Ser Leu Leu Ile Asp Gly Trp Ser Leu Glu Lys Lys Ile
            180                 185                 190

Ser Ile Asn Asp Ala Ser Met Leu Arg Glu Met Ala Trp Lys Arg Asp
            195                 200                 205

Asn Arg Leu Arg Glu Ala Tyr Leu Ser Ser Arg Gly Met Glu Glu Arg
            210                 215                 220

Glu Leu Ile Asp Ser Phe Leu Lys Met Ala Leu Pro Gly Thr Ser Ser
225                 230                 235                 240

Gly Leu His Ile Val His Ile Ala Ala Glu Met Ala Pro Val Ala Lys
                245                 250                 255

Val Gly Gly Leu Ala Asp Val Ile Ser Gly Leu Gly Lys Ala Leu Gln
            260                 265                 270

Lys Lys Gly His Leu Val Glu Ile Ile Leu Pro Lys Tyr Asp Cys Met
            275                 280                 285

Gln His Asn Gln Ile Asn Asn Leu Lys Val Leu Asp Val Val Val Lys
            290                 295                 300

Ser Tyr Phe Glu Gly Asn Met Phe Ala Asn Lys Ile Trp Thr Gly Thr
305                 310                 315                 320

Val Glu Gly Leu Pro Val Tyr Phe Ile Glu Pro Gln His Pro Gly Lys
                325                 330                 335

Phe Phe Trp Arg Ala Gln Tyr Tyr Gly Glu His Asp Asp Phe Lys Arg
            340                 345                 350

Phe Ser Tyr Phe Ser Arg Val Ala Leu Glu Leu Leu Tyr Gln Ser Gly
            355                 360                 365

Lys Lys Val Asp Ile Ile His Cys His Asp Trp Gln Thr Ala Phe Val
            370                 375                 380

Ala Pro Leu Tyr Trp Asp Val Tyr Ala Asn Leu Gly Phe Asn Ser Ala
385                 390                 395                 400

Arg Ile Cys Phe Thr Cys His Asn Phe Glu Tyr Gln Gly Ile Ala Pro
                405                 410                 415

Ala Gln Asp Leu Ala Tyr Cys Gly Leu Asp Val Asp His Leu Asp Arg
            420                 425                 430

Pro Asp Arg Met Arg Asp Asn Ser His Gly Arg Ile Asn Val Val Lys
            435                 440                 445

Gly Ala Val Val Tyr Ser Asn Ile Val Thr Thr Val Ser Pro Thr Tyr
450                 455                 460

Ala Gln Glu Val Arg Ser Glu Gly Gly Arg Gly Leu Gln Asp Thr Leu
465                 470                 475                 480

Lys Val His Ser Lys Lys Phe Val Gly Ile Leu Asn Gly Ile Asp Thr
                485                 490                 495

Asp Thr Trp Asn Pro Ser Thr Asp Arg Phe Leu Lys Val Gln Tyr Ser
            500                 505                 510

Ala Asn Asp Leu Tyr Gly Lys Ser Ala Asn Lys Ala Leu Arg Lys
            515                 520                 525

Gln Leu Lys Leu Ala Ser Thr Gln Ala Ser Gln Pro Leu Val Gly Cys
            530                 535                 540

Ile Thr Arg Leu Val Pro Gln Lys Gly Val His Leu Ile Arg His Ala
545                 550                 555                 560

Ile Tyr Lys Ile Thr Glu Leu Gly Gly Gln Phe Val Leu Leu Gly Ser
                565                 570                 575

Ser Pro Val Gln His Ile Gln Arg Glu Phe Glu Gly Ile Ala Asp Gln
            580                 585                 590
```

```
Phe Gln Asn Asn Asn Asn Val Arg Leu Leu Leu Lys Tyr Asp Asp Ala
        595                 600                 605

Leu Ala His Met Ile Phe Ala Ala Ser Asp Met Phe Ile Val Pro Ser
        610                 615                 620

Met Phe Glu Pro Cys Gly Leu Thr Gln Met Val Ala Met Arg Tyr Gly
625                 630                 635                 640

Ser Val Pro Val Val Arg Arg Thr Gly Gly Leu Asn Asp Ser Val Phe
                645                 650                 655

Asp Leu Asp Asp Glu Thr Ile Pro Met Glu Val Arg Asn Gly Phe Thr
            660                 665                 670

Phe Leu Lys Ala Asp Glu Gln Asp Phe Gly Asn Ala Leu Glu Arg Ala
        675                 680                 685

Phe Asn Tyr Tyr His Arg Lys Pro Glu Val Trp Lys Gln Leu Val Gln
        690                 695                 700

Lys Asp Met Lys Ile Asp Phe Ser Trp Asp Thr Ser Val Ser Gln Tyr
705                 710                 715                 720

Glu Glu Ile Tyr Gln Lys Thr Ala Thr Arg Ala Arg Ala Ala Ala
                725                 730                 735
```

NUCLEIC ACID MOLECULES FROM PLANTS CODING ENZYMES WHICH PARTICIPATE IN THE STARCH SYNTHESIS

This application is a DIV of U.S. application Ser. No. 09/115,704, filed Jul. 15, 1998, now U.S. Pat. No. 6,211,436, which is a CON of PCT/EP97/00158, filed Jan. 15, 1997.

FIELD OF THE INVENTION

The present invention relates to nucleic acid molecules encoding an enzyme participating in the starch synthesis in plants. This enzyme is a novel isotype of the starch synthase. Furthermore, this invention relates to vectors, bacteria as well as to plant cells transformed with the described nucleic acid molecules and to plants which may be obtained from these plant cells by means of regeneration.

Furthermore, methods for the production of transgenic plants are described, which due to the introduction of DNA molecules encoding a starch synthase synthesize a starch modified in its properties.

With respect to the increasing significance which has recently been ascribed to vegetal substances as regenerative sources of raw materials, one of the objects of biotechnological research is trying to adapt vegetal raw materials to the demands of the processing industry. In order to enable the use of regenerative raw materials in as many areas as possible, it is furthermore important to obtain a large variety of substances. Apart from oils, fats and proteins, polysaccharides constitute the essential regenerative raw materials derived from plants. Apart from cellulose, starch maintains an important position among the polysaccharides, being one of the most significant storage substances in higher plants. Among those, maize is one of the most interesting plants as it is the most important cultivated plant for the production of starch.

The polysaccharide starch is a polymer made up of chemically homogeneous basic components, namely the glucose molecules. However, it constitutes a highly complex mixture of various types of molecules which differ from each other in their degree of polymerization and in the degree of branching of the glucose chains. Therefore, starch is not a homogeneous raw material. One differentiates particularly between amylose-starch, a basically non-branched polymer made up of α-1,4-glycosidically branched glucose molecules, and amylopectin-starch which in turn is a complex mixture of various branched glucose chains. The branching results from additional α-1,6-glycosidic interlinkings. In plants used typically for the production of starch, such as maize or potato, the synthesized starch consists of approximately 25% amylose-starch and of about 75% amylopectin-starch.

In order to enable as wide a use of starch as possible, it seems to be desirable that plants be provided which are capable of synthesizing modified starch which is particularly suitable for various uses. One possibility to provide such plants—apart from breeding methods—is the specific genetic modification of the starch metabolism of starch-producing plants by means of recombinant DNA techniques. However, a prerequisite therefore is to identify and to characterize the enzymes involved in the starch synthesis and/or the starch modification as well as to isolate the respective DNA molecules encoding these enzymes.

The biochemical pathways which lead to the synthesis of starch are basically known. The starch synthesis in plant cells takes place in the plastids. In photosynthetically active tissues these are the chloroplasts, in photosynthetically inactive, starch-storing tissues the amyloplasts.

The most important enzymes involved in starch synthesis are starch synthases as well as branching enzymes. In the case of starch synthases various isotypes are described which all catalyze a polymerization reaction by transferring a glucosyl residue of ADP-glucose to α-1,4-glucans. Branching enzymes catalyze the introduction of α-1,6 branchings into linear α-1,4-glucans.

Starch synthases may be divided up in two groups: the granule-bound starch synthases (GBSS) and the soluble starch synthases (SSS). This distinction is not always evident since some starch synthases are granule-bound as well as soluble (Denyer et al., Plant J. 4 (1993), 191–198; Mu et al., Plant J. 6 (1994), 151–159). Within these classifications, various isotypes are described for various species of plants. These isotypes differ from each other in their dependency on primer molecules (so-called "primer dependent" (type II) and "primer independent" (type I) starch synthases).

So far only in the case of the isotype GBSS I its exact function during starch synthesis has been successfully determined. Plants in which this enzyme activity has been strongly or completely reduced, synthesize starch free of amylose (a so-called "waxy" starch) (Shure et al., Cell 35 (1983), 225–233; Visser et al., Mol. Gen. Genet. 225 (1991), 289–296; WO 92/11376); therefore this enzyme has been assigned a decisive role in synthesizing amylose-starch. This phenomenon is also observed in the cells of the green alga Chlamydomonas reinhardtii (Delrue et al., J. Bacteriol. 174 (1992), 3612–3620). In the case of Chlamydomonas it was furthermore demonstrated that GBSS I is not only involved in the synthesis of amylose but also has a certain influence on amylopectin synthesis. In mutants which do not show any GBSS I activity a certain fraction of the normally synthesized amylopectin, exhibiting long chain glucans, is missing.

The functions of the other isotypes of the granule-bound starch synthases, particularly GBSS II, and of the soluble starch synthases are so far not clear. It is assumed that soluble starch synthases, together with branching enzymes, are involved in the synthesis of amylopectin (see e.g. Ponstein et al., Plant Physiol. 92 (1990), 234–241) and that they play an important role in the regulation of starch synthesis rate.

In the case of maize, two isotypes of the starch granule-bound starch synthase as well as two or respectively three isotypes of the soluble starch synthases were identified (Hawker et al., Arch. Biochem. Biophys. 160 (1974), 530–551; Pollock and Preiss, Arch. Biochem. Biophys. 204 (1980), 578–588; MacDonald and Preiss, Plant Physiol. 78 (1985), 849–852; Mu et al., Plant J. 6 (1994), 151–159).

A cDNA encoding GBSS I from maize and a genomic DNA have already been described (Shure et al., Cell 35 (1983), 225–233; Kloesgen et al., Mol. Gen. Genet. 203 (1986), 237–244). Moreover, a so-called "expressed sequence tag" (EST) has been described (Shen et al., 1994, GenBank No.: T14684); the amino acid sequence derived therefrom has a strong similarity to the amino acid sequence derived from the GBSS II from pea (Dry et al., Plant J. 2 (1992), 193–202) and potato (Edwards et al., Plant J. 8 (1995), 283–294). Nucleic acid sequences encoding further starch synthase-isotypes from maize are yet unknown. cDNA sequences encoding starch synthases other than GBSS I have so far only been described for pea (Dry et al., Plant J. 2 (1992), 193–202), rice (Baba et al., Plant Physiol. 103 (1993), 565–573) and potatoes (Edwards et al., Plant J. 8 (1995), 283–294).

Soluble starch synthases have been identified in several other plant species apart from maize. Soluble starch synthases have for example been isolated in homogeneous form from pea (Denyer and Smith, Planta 186 (1992), 609–617) and potatoes (Edwards et al., Plant J. 8 (1995), 283–294). In these cases it was found that the isotype of the soluble starch synthase identified as SSS II is identical with the granule-bound starch synthase GBSS II (Denyer et al., Plant J. 4 (1993), 191–198; Edwards et al., Plant J. 8 (1995), 283–294). In the case of some other plant species the existence of several SSS-isotypes was described by means of chromatographic methods, as for example in the case of barley (Tyynelä and Schulman, Physiologia Plantarum 89 (1993) 835–841; Kreis, Planta 148 (1980), 412–416) and wheat (Rijven, Plant Physiol. 81 (1986), 448–453). However, DNA sequences encoding these proteins have so far not been described.

In order to provide further possibilities for modifying any desired starch-storing plant in such a way that it will synthesize a modified starch, respective DNA sequences encoding further isotypes of starch synthases have to be identified.

Therefore, the technical problem underlying the present invention is to provide nucleic acid molecules encoding enzymes involved in starch biosynthesis and by means of which genetically modified plants may be produced that show an elevated or reduced activity of those enzymes, thereby prompting a modification in the chemical and/or physical properties of the starch synthesized in these plants.

This problem has been solved by the provision of the embodiments described in the claims.

SUMMARY OF THE INVENTION

Therefore, the present invention relates to nucleic acid molecules encoding proteins with the biological activity of a starch synthase, wherein such molecules preferably encode proteins which comprise the amino acid sequence depicted under Seq ID No. 2. The invention particularly relates to nucleic acid molecules which comprise all or part of the nucleotide sequence mentioned under Seq ID No. 1, preferably molecules, which comprise the coding region indicated in Seq ID No. 1 or, as the case may be, corresponding ribonucleotide sequences. Nucleic acid molecules that encode a starch synthase and the sequence of which differs from the nucleotide sequences of the above-mentioned molecules due to the degeneracy of the genetic code are also the subject-matter of the invention.

The present invention further relates to nucleic acid molecules encoding a starch synthase and hybridizing to one of the above-mentioned molecules.

The invention also relates to nucleic acid molecules showing a sequence which is complementary to the whole or to a part of the sequence of the above-mentioned nucleic acid molecules.

DETAILED DESCRIPTION OF THE INVENTION

The nucleic acid molecules of the invention may be DNA as well as RNA molecules. Corresponding DNA molecules are for instance genomic or cDNA molecules. The RNA molecules may for example be MRNA or antisense RNA molecules.

Within the framework of the present invention the term "hybridization" signifies hybridization under conventional hybridizing conditions, preferably under stringent conditions, as described for example in Sambrook et al., Molecular Cloning, A Laboratory Manual, 2nd Edition (1989) Cold Spring Harbor Laboratory Press, Cold Spring Harbor, N.Y.). Nucleic acid molecules hybridizing to the nucleic acid molecules of the invention may basically be derived from any desired type of organism (i.e. prokaryotes or eukaryotes, in particular from bacteria, fungi, algae, plants or animal organisms) comprising such molecules. They are preferably derived from monocotyledonous or dicotyledonous plants, in particular from useful plants, and particularly preferred from starch-storing plants, in particular from maize.

Nucleic acid molecules hybridizing to the molecules of the invention may for example be isolated from genomic or cDNA libraries of various organisms.

The identification and isolation of such nucleic acid molecules from plants and other organisms may take place by using the molecules of the invention or parts of these molecules or, as the case may be, the reverse complements of these molecules, e.g. by hybridization according to standard methods (see e.g. Sambrook et al., 1989, Molecular Cloning, A Laboratory Manual, 2nd Edition, Cold Spring Harbor Laboratory Press, Cold Spring Harbor, N.Y.).

As a probe for hybridization e.g. nucleic acid molecules may be used which exactly or basically contain the nucleotide sequence indicated under Seq ID No. 1 or parts thereof. The fragments used as hybridization probe may also be synthetic fragments which were produced by means of the conventional synthesizing methods and the sequence of which is basically identical with that of a nucleic acid molecule of the invention. After identifying and isolating the genes hybridizing to the nucleic acid sequences of the invention, the sequence has to be determined and the properties of the proteins encoded by this sequence have to be analyzed.

The molecules hybridizing to the nucleic acid molecules of the invention also comprise fragments, derivatives and allelic variants of the above-described nucleic acid molecules which encode a protein according to the invention. In this context, fragments are defined as parts of the nucleic acid molecules, which are long enough in order to encode one of the described proteins. In this context, the term derivative means that the sequences of these molecules differ from the sequences of the above-mentioned nucleic acid molecules at one or more positions and that they exhibit a high degree of homology to these sequences. In this regard, homology means a sequence identity of at least 40%, in particular an identity of at least 60%, preferably of more than 80% and still more preferably a sequence identity of more than 90%. The deviations occurring when comparing with the above-described nucleic acid molecules might have been caused by deletion, substitution, insertion or recombination.

Moreover, homology means that functional and/or structural equivalence exists between the respective nucleic acid molecules or the proteins they encode. The nucleic acid molecules, which are homologous to the above-described molecules and represent derivatives of these molecules, are generally variations of these molecules, that constitute modifications which exert the same biological function. These variations may be naturally occurring variations, for example sequences derived from other organisms, or mutations, wherein these mutations may have occurred naturally or they may have been introduced by means of a specific mutagenesis. Moreover the variations may be synthetically produced sequences. The allelic variants may be naturally occurring as well as synthetically produced variants or variants produced by recombinant DNA techniques.

The proteins encoded by the various variants of the nucleic acid molecules according to the invention exhibit certain common characteristics. Enzyme activity, molecular weight, immunologic reactivity, conformation etc. may belong to these characteristics as well as physical properties such as the mobility in gel electrophoresis, chromatographic characteristics, sedimentation coefficients, solubility, spectroscopic properties, stability; pH-optimum, temperature-optimum etc.

Significant characteristics of a starch synthase are: i) its localization within the stroma of the plastids of plant cells; ii) its capability of synthesizing linear α-1,4-linked polyglucans using ADP-glucose as substrate. This activity can be determined as shown in Denyer and Smith (Plants 186 (1992), 606–617) or as described in the examples.

The nucleic acid molecules of the invention may in principle be derived from any desired organism expressing the described proteins, preferably from plants and in particular from starch-synthesizing or starch-storing plants. They may be monocotyledonous as well as dicotyledonous plants. Cereals (such as barley, rye, oats, wheat etc.), maize, rice, pea, cassava or potato etc. are particularly preferred.

The proteins encoded by the nucleic acid molecules of the invention represent a so far not identified and not characterized isotype of a plant starch synthase. These proteins exhibit the enzymatic activity of a starch synthase as well as certain regions of homology to starch synthases from plants known so far; however, they may not be unambiguously classified as any of the isotypes known so far. In particular, the proteins encoded by the nucleic acid molecules of the invention have the property that they lead to a blue staining of the bacterial colonies after their introduction into an *E.coli* mutant, in which all glg genes are deleted and which expresses a mutated, deregulated ADP glucose-pyrophosphorylase, cultivation of this mutant on a glucose-containing medium and staining with iodine vapor.

Another subject matter of the invention are oligonucleotides which hybridize specifically with a nucleic acid molecule of the invention. Such oligonucleotides preferably have a length of at least 10, in particular of at least 15 and particularly preferred of at least 50 nucleotides. These oligonucleotides are characterized in that they specifically hybridize with the nucleic acid molecules of the invention, i.e. that they do not or only to a very limited extent hybridize with nucleic acid sequences encoding other proteins, in particular other starch synthases. The oligonucleotides of the invention may for example be used as primers for a PCR reaction. They may also be components of antisense constructs or of DNA molecules encoding suitable ribozymes.

Furthermore, the invention relates to vectors, especially plasmids, cosmids, viruses, bacteriophages and other vectors common in genetic engineering, which contain the above-mentioned nucleic acid molecules of the invention.

In a preferred embodiment the nucleic acid molecules contained in the vectors are linked to regulatory elements that ensure the transcription and synthesis of a translatable RNA in prokaryotic and eukaryotic cells.

The expression of the nucleic acid molecules of the invention in prokaryotic cells, e.g. in *Escherichia coli*, is interesting insofar as this enables a more precise characterization of the enzymatic activities of the enzymes encoding these molecules. In particular, it is possible to characterize the product being synthesized by the respective enzymes in the absence of other enzymes which are involved in the starch synthesis of the plant cell. This makes it possible to draw conclusions about the function, which the respective protein exerts during the starch synthesis within the plant cell.

Moreover, it is possible to introduce various mutations into the nucleic acid molecules of the invention by means of conventional molecular-biological techniques (see e.g. Sambrook et al., 1989, Molecular Cloning, A Laboratory Manual, 2nd Edition, Cold Spring Harbor Laboratory Press, Cold Spring Harbor, N.Y.), whereby the synthesis of proteins with possibly modified biological properties can be achieved. By means of this it is on the one hand possible to produce deletion mutants, in which nucleic acid molecules are produced by continuing deletions at the 5'- or the 3'-end of the encoding DNA-sequence. These nucleic acid molecules may lead to the synthesis of correspondingly shortened proteins. Such deletions at the 5'-end of the nucleotide sequence make it possible, for example, to identify amino acid sequences which are responsible for the translocation of the enzyme in the plastids (transit peptides). This allows for the specific production of enzymes which due to the removal of the respective sequences are no longer located in the plastids but within the cytosole, or which due to the addition of other signal sequences are located in other compartments.

On the other hand point mutations might also be introduced at positions where a modification of the amino acid sequence influences, for example, the enzyme activity or the regulation of the enzyme. In this way e.g. mutants with a modified $K_m$-value may be produced, or mutants which are no longer subject to the regulation mechanisms by allosteric regulation or covalent modification usually occurring in cells.

Furthermore, mutants may be produced exhibiting a modified substrate or product specificity such as mutants that use ADP-glucose-6-phosphate instead of ADP-glucose as substrate. Moreover, mutants with a modified activity-temperature-profile may be produced.

For the genetic manipulation in prokaryotic cells the nucleic acid molecules of the invention or parts of these molecules may be integrated into plasmids which allow for a mutagenesis or a sequence modification by recombination of DNA sequences. By means of standard methods (cf. Sambrook et al., 1989, Molecular Cloning: A laboratory manual, 2nd edition, Cold Spring Harbor Laboratory Press, N.Y., USA) base exchanges may be carried out or natural or synthetic sequences may be added. In order to connect the DNA fragments, adapters or linkers may be attached to the fragments. Moreover, use can be made of manipulations which offer suitable restriction sites or which remove superfluous DNA or restriction sites. Wherever use is made of inserts, deletions or substitutions, in vitro mutagenesis, "primer repair", restriction or ligation may be used. For analyzing use is usually made of a sequence analysis, a restriction analysis or further biochemico-molecularbiological methods.

In a further embodiment the invention relates to host cells, in particular prokaryotic or eukaryotic cells, which have been transformed and genetically modified by an above-mentioned nucleic acid molecule of the invention or by a vector of the invention, as well as cells derived from such transformed cells and containing a nucleic acid molecule or a vector of the invention. This is preferably a bacterial cell or a plant cell.

Furthermore, the proteins encoded by the nucleic acid molecules of the invention or biologically active fragments thereof are the subject-matter of the invention as well as methods for their production wherein a host cell of the invention is cultivated under conditions that allow for the synthesis of the protein and wherein the protein is then isolated from the cultivated cells and/or the culture medium.

By the provision of the nucleic acid molecules of the invention it is now possible—by means of recombinant DNA techniques—to specifically interfere with the starch metabolism of plants in a way so far impossible by means of breeding. Thereby, the starch metabolism may be modified in such a way that a modified starch is synthesized which e.g. is modified, compared to the starch synthesized in wildtype plants, with respect to its physico-chemical properties, especially the amylose/amylopectin ratio, the degree of branching, the average chain length, the phosphate content, the pastification behavior, the size of the starch granules and/or the shape of the starch granules. There is the possibility of increasing the yield of genetically modified plants by increasing the activity of the proteins described in the invention, e.g. by overexpressing the respective nucleic acid molecules or by making mutants available which are no longer subject to cell-specific regulation schemes and/or different temperature-dependencies with respect to their activity. The economic significance of the chance to interfere with the starch synthesis of maize alone is obvious since 80% of all starch produced annually in the world is produced from starch.

Therefore, it is possible to express the nucleic acid molecules of the invention in plant cells in order to increase the activity of the respective starch synthase. Furthermore, the nucleic acid molecules of the invention may be modified by means of methods known to the skilled person, in order to produce starch synthases according to the invention which are no longer subject to the cell-specific regulation mechanisms or show modified temperature-dependencies or substrate or product specificities.

In expressing the nucleic acid molecules of the invention in plants the synthesized proteins may in principle be located in any desired compartment within the plant cell. In order to locate it within a specific compartment, the sequence ensuring the localization in the plastids must be deleted and the remaining coding region optionally has to be linked to DNA sequences which ensure localization in the respective compartment. Such sequences are known (see e.g. Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

Thus, the present invention also relates to transgenic plant cells transformed and genetically modified with a nucleic acid molecule of the invention, as well as it relates to transgenic plant cells which are derived from cells transformed in such a way. Such cells contain a nucleic acid molecule of the invention, wherein this is preferably linked to regulatory DNA elements, which ensure the transcription in plant cells, especially with a promoter. The transgenic plant cells of the invention differ from naturally occurring plant cells in that they contain integrated into their genome a DNA molecule of the invention which either does not naturally occur in such cells at all or only in a different genomic environment, i.e. at a different position in the genome. Plant cells which may contain naturally in their genome a DNA molecule of the invention differ from the plant cells of the invention in that the latter exhibit more gene copies of the nucleic acid molecules of the invention than would naturally occur in the respective naturally occurring plant cells and in that these additional copies are integrated at different genetic positions. The above-mentioned features may for example be determined by means of Southern Blot analysis of genomic DNA. By means of methods known to the skilled person the transgenic plant cells can be regenerated to whole plants. Thus, the plants obtained by regenerating the transgenic plant cells of the invention are also the subject-matter of the present invention. A further subject-matter of the invention are plants which contain the above-described transgenic plant cells. The transgenic plants may in principle be plants of any desired species, i.e. they may be monocotyledonous as well as dicotyledonous plants. They are preferably useful plants, in particular starch-synthesizing or starch-storing plants such as cereals (rye, barley, oats, wheat etc.), rice, maize, peas, cassava or potatoes.

The invention also relates to propagation material of the plants of the invention, e.g. fruits, seeds, tubers, rootstocks, seedlings, cuttings etc.

Due to the expression or, as the case may be, additional expression of a nucleic acid molecule of the invention, the transgenic plant cells and plants described in the invention synthesize a starch which compared to starch synthesized in wildtype plants is modified for example in its physico-chemical properties, in particular in the amylose/amylopectin ratio, the degree of branching, the average chain-length, the phosphate content, the pastification behavior, the size of the starch granules and/or the shape of the starch granules. Compared with wildtype-starch, such starch may be modified in particular with respect to its viscosity and/or the gel formation properties of the glues of this starch.

Thus, also the starch obtainable from transgenic plant cells and plants according to the invention is the subject-matter of the present invention.

By means of the nucleic acid molecules of the invention it is furthermore possible to produce plant cells and plants in which the activity a protein of the invention is reduced. This also leads to the synthesis of a starch with modified chemical and/or physical properties when compared to the starch from wildtype plant cells.

Thus, transgenic plant cells, in which the activity of a protein according to the invention is reduced when compared to non-transformed plants, are a further subject-matter of the invention.

The production of plant cells with a reduced activity of a protein of the invention may for example be achieved by the expression of a corresponding antisense-RNA, of a sense-RNA for achieving a cosuppression effect or the expression of a correspondingly constructed ribozyme, which specifically cleaves transcripts encoding one of the proteins of the invention, using the nucleic acid molecules of the invention.

In order to reduce the activity of a protein of the invention antisense-RNA is preferably expressed in plant cells.

In order to express an antisense-RNA, on the one hand DNA molecules can be used which comprise the complete sequence encoding a protein of the invention, including possibly existing flanking sequences as well as DNA molecules, which only comprise parts of the coding region. These parts have to be long enough in order to prompt an antisense-effect within the cells. Basically, sequences with a minimum length of 15 bp, preferably with a length of 100–500 bp and for an efficient antisense-inhibition, in particular sequences with a length of more than 500 bp may be used. Generally DNA-molecules are used which are shorter than 5000 bp, preferably sequences with a length of less than 2500 bp.

Use may also be made of DNA sequences which are highly homologous, but not completely identical to the sequences of the DNA molecules of the invention. The minimal homology should be more than about 65%. Preferably, use should be made of sequences with homologies between 95 and 100%.

The cells of the invention differ from naturally occurring cells in that they contain a heterologous recombinant DNA molecule encoding an antisense RNA, a ribozyme or a cosuppression RNA. Due to the expression of this heterologous recombinant DNA molecule the synthesis of a protein of the invention in the cells is reduced and thereby also the corresponding activity.

In this context "heterologous" DNA means that the DNA introduced into the cells is a DNA not naturally occurring in the cells in this form. On the one hand, it may be DNA which does naturally not at all occur in these transformed cells or DNA which, even if it does occur in these cells, is integrated at other genetic positions as exogenous DNA and is therefore situated within another genetic environment.

The transgenic plant cells of the invention can be regenerated to whole plants by means of methods known to the skilled person. Thus, plants containing the transgenic plant cells of the invention are also the subject-matter of the present invention. These plants may in principal be plants of any desired plant species, i.e. monocotyledonous as well as dicotyledonous plants. Preferably, they are useful plants, i.e. plants cultivated by man for the nourishment of humans or animals or for technical purposes. Particularly preferred, they are starch-synthesizing or starch-storing plants such as cereals (rye, barley, oats, wheat, etc.), rice, maize, pea, cassava or potato. The invention also relates to propagation material of the plants of the invention such as fruits, seeds, tubers, rootstocks, seedlings, cuttings etc.

Due to the reduction of the activity of a protein of the invention, the transgenic plant cells and plants of the invention synthesize a starch which is modified, compared to the starch synthesized in wildtype plants, for example, in its physico-chemical properties, in particular in the amylose/amylopectin ratio, the degree of branching, the average chain-length, the phosphate-content, the pastification behavior, the size of the starch granules and/or the shape of the starch granules. This starch may for example exhibit modified viscosities and/or gel formation properties of its glues when compared to starch derived from wildtype plants. Thus, starch obtainable from the above-mentioned transgenic plant cells and plants also is the subject-matter of the present invention.

The starches of the invention may be modified according to techniques known to the skilled person; in unmodified as well as in modified form they are suitable for the use in foodstuffs and for the use in non-foodstuffs.

Basically, the possibilities of uses of the starch can be subdivided into two major fields. One field comprises the hydrolysis products of starch, essentially glucose and glucans components obtained by enzymatic or chemical processes. They can be used as starting material for further chemical modifications and processes, such as fermentation. In this context, it might be of importance that the hydrolysis process can be carried out simply and inexpensively. Currently, it is carried out substantially enzymatically using amyloglucosidase. It is thinkable that costs might be reduced by using lower amounts of enzymes for hydrolysis due to changes in the starch structure, e.g. increasing the surface of the grain, improved digestibility due to less branching or a steric structure, which limits the accessibility for the used enzymes.

The other field in which the starch is used because of its polymer structure as so-called native starch, can be subdivided into two further areas:

1. Use in foodstuffs

Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions.

A preferred area of application of native starch is the field of bakery-goods and pasta.

2. Use in non-foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

2.1 Paper and cardboard industry

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

2.2 Adhesive industry

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

2.3 Textile and textile care industry

Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

2.4 Building industry

The fourth area of application of starch is its use as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

2.5 Ground stabilization

Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

2.6 Use of starch in plant protectives and fertilizers

Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

2.7 Drugs, medicine and cosmetics industry

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

2.8 Starch as an additive in coal and briquettes

The use of starch as an additive in coal and briquettes is also thinkable. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, the starch is suitable as a binding agent since adding it to coal and briquette can considerably reduce the emission of toxic substances.

2.9 Processing of ore and coal slurry

Furthermore, the starch may be used as a flocculant in the processing of ore and coal slurry.

2.10 Starch as an additive in casting

Another field of application is the use as an additive to process materials in casting. For various casting processes cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfill more prerequisites for the production process, such as dispersability in cold water, rehydratisability, good mixability in sand and high capability of binding water.

2.11 Use of starch in rubber industry

In the rubber industry starch may be used for improving the technical and optical quality. Reasons for this are improved surface gloss, grip and appearance. For this purpose, the starch is dispersed on the sticky rubberized surfaces of rubber substances before the cold vulcanization. It may also be used for improving the printability of rubber.

2.12 Production of leather substitutes

Another field of application for the modified starch is the production of leather substitutes.

2.13 Starch in synthetic polymers

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved antiblock behavior as well as improved printability with aqueous dyes.

Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. These super absorbers are used mainly in the hygiene field, e.g. in products such as diapers and sheets, as well as in the agricultural sector, e.g. in seed pellets.

What is decisive for the use of the new starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding film formation, adhesive strength, enzyme stability, digestibility and reactivity.

The production of modified starch by genetically operating with a transgenic plant may modify the properties of the starch obtained from the plant in such a way as to render further modifications by means of chemical or physical methods superfluous. On the other hand, the starches modified by means of recombinant DNA techniques might be subjected to further chemical modification, which will result in further improvement of the quality for certain of the above-described fields of application. These chemical modifications are principally known to the person skilled in the art. These are particularly modifications by means of heat treatment
acid treatment
oxidation and
esterification leading to the formation of phosphate, nitrate, sulfate, xanthate, acetate and citrate starches. Other organic acids may also be used for the esterification:

formation of starch ethers starch alkyl ether, O-allyl ether, hydroxylalkyl ether, O-carboxylmethyl ether, N-containing starch ethers, P-containing starch ethers and S-containing starch ethers.

formation of branched starches
formation of starch graft polymers.

In order to express the nucleic acid molecules of the invention in sense- or antisense-orientation in plant cells, these are linked to regulatory DNA elements which ensure the transcription in plant cells. Such regulatory DNA elements are particularly promoters. Basically any promoter which is active in plant cells may be used for the expression.

The promoter may be selected in such a way that the expression takes place constitutively or only in a certain tissue, at a certain point of time of the plant development or at a point of time determined by external factors. With respect to the plant the promoter may be homologous or heterologous. Suitable promoters for a constitutive expression are, e.g. the 35S RNA promoter of the Cauliflower Mosaic Virus and the ubiquitin promoter from maize. For a tuber-specific expression in potatoes the patatin gene promoter B33 (Rocha-Sosa et al., EMBO J. 8 (1989), 23–29) may be used or a promoter can be used which ensures expression only in photosynthetically active tissues, e.g. the ST-LS1 promoter (Stockhaus et al., Proc. Natl. Acad. Sci. USA 84 (1987), 7943–7947; Stockhaus et al., EMBO J. 8 (1989), 2445–2451). For an endosperm-specific expression the HMG promoter from wheat, the USP promoter, the phaseolin promoter or promoters from zein genes from maize are suitable.

Furthermore, a termination sequence may be present, which serves to correctly end the transcription and to add a poly-A-tail to the transcript which is believed to stabilize the transcripts. Such elements are described in the literature (cf. Gielen et al., EMBO J. 8 (1989), 23–29) and can be exchanged as desired.

The present invention provides nucleic acid molecules encoding a novel isotype of a starch synthase identified in maize. This allows for the identification of the function of this isotype in the starch biosynthesis as well as for the production of genetically modified plants in which the activity of this enzyme is modified. This enables the synthesis of starch with a modified structure and therefore with modified physico-chemical properties in the plants manipulated in such a way. In principal, the nucleic acid molecules of the invention may also be used in order to produce plants in which the activity of the starch synthase of the invention is elevated or reduced and in which at the same time the activities of other enzymes involved in the starch biosynthesis are modified. Thereby, all kinds of combinations and permutations are thinkable. By modifying the activity of one or more isotypes of the starch synthases in plants, a synthesis of a starch modified in its structure is brought about. By increasing the activity of one or more isotypes of the starch synthases in the cells of the starch-storing tissue of transformed plants, such as in the endosperm of maize or wheat or in the potato tuber, increased yields may be the result. For example, nucleic acid molecules encoding a protein of the invention, or corresponding antisense-constructs may be introduced into plant cells in which the synthesis of endogenous GBSS I-, SSS- or GBSS II-proteins is already inhibited due to an antisense-effect or a mutation, or in which the synthesis of the branching enzyme is inhibited (as described e.g. WO92/14827 or in connection with the ae mutant (Shannon and Garwood, 1984, in Whistler, BeMiller and Paschall, Starch: Chemistry and Technology, Academic Press, London, $2^{nd}$ edition: 25–86)).

If the inhibition of the synthesis of several starch synthases in transformed plants is to be achieved, DNA molecules can be used for transformation, which at the same time contain several regions in antisense-orientation controlled by a suitable promoter and encoding the corresponding starch synthases. In such constructs, each sequence may alternatively be controlled by its own promoter or else the sequences may be transcribed as a fusion from a common promoter. The last alternative will generally be preferred as in this case the synthesis of the respective proteins should be inhibited to approximately the same extent.

Furthermore it is possible to construct DNA molecules in which apart from DNA sequences encoding starch synthases other DNA sequences are present encoding other proteins involved in the starch synthesis or modification and coupled to a suitable promoter in antisense orientation. Again, the sequences may be connected up in series and be transcribed from a common promoter. For the length of the individual coding regions used in such a construct the above-mentioned facts concerning the production of antisense-construct are also true. There is no upper limit for the number of antisense fragments transcribed from a promoter in such a DNA molecule. The resulting transcript, however, should not be longer than 10 kb, preferably 5 kb.

Coding regions which are located in antisense-orientation behind a suitable promoter in such DNA molecules in combination with other coding regions, may be derived from DNA sequences encoding the following proteins: granule-bound starch synthases (GBSS I and II), other soluble starch synthases (SSS I and II), branching enzymes, debranching enzymes, disproportionizing enzymes and starch phosphorylases. This enumeration merely serves as an example. The use of other DNA sequences within the framework of such a combination is also thinkable.

By means of such constructs it is possible to inhibit the synthesis of several enzymes at the same time within the plant cells transformed with these molecules.

Furthermore, the constructs may be introduced into classical mutants which are defective for one or more genes of the starch biosynthesis (Shannon and Garwood, 1984, in Whistler, BeMiller and Paschall, Starch: Chemistry and Technology, Academic Press, London, $2^{nd}$ edition: 25–86). These defects may be related to the following proteins: granule-bound (GBSS I and II) and soluble starch synthases (SSS I and II), branching enzymes (BE I and II), debranching enzymes (R-enzymes), disproportionizing enzymes and starch phosphorylases. This enumeration merely serves as an example.

By means of such strategy it is furthermore possible to inhibit the synthesis of several enzymes at the same time within the plant cells transformed with these molecules. In order to prepare the introduction of foreign genes into higher plants a high number of cloning vectors are at disposal, containing a replication signal for E.coli and a marker gene for the selection of transformed bacterial cells. Examples for such vectors are pBR322, pUC series, M13mp series, pACYC184 etc. The desired sequence may be integrated into the vector at a suitable restriction site. The obtained plasmid is used for the transformation of E.coli cells. Transformed E.coli cells are cultivated in a suitable medium and subsequently harvested and lysed. The plasmid is recovered. As an analyzing method for the characterization of the obtained plasmid DNA use is generally made of restriction analysis, gel electrophoresis and other biochemico-molecularbiological methods. After each manipulation the plasmid DNA may be cleaved and the obtained DNA fragments may be linked to other DNA sequences. Each plasmid DNA may be cloned into the same or in other plasmids.

In order to introduce DNA into a plant host cell a wide range of techniques are at disposal. These techniques comprise the transformation of plant cells with T-DNA by using Agrobacterium tumefaciens or Agrobacterium rhizogenes as transformation medium, the fusion of protoplasts, the injection and the electroporation of DNA, the introduction of DNA by means of the biolistic method as well as further possibilities.

In the case of injection and electroporation of DNA into plant cells, there are no special demands made to the plasmids used. Simple plasmids such as pUC derivatives may be used. However, in case that whole plants are to be regenerated from cells transformed in such a way, a selectable marker gene should be present.

Depending on the method of introducing desired genes into the plant cell, further DNA sequences may be necessary. If the Ti- or Ri-plasmid is used e.g. for the transformation of the plant cell, at least the right border, more frequently, however, the right and left border of the Ti- and Ri-plasmid T-DNA should be connected to the foreign gene to be introduced as a flanking region.

If Agrobacteria are used for the transformation, the DNA which is to be integrated must be cloned into special plasmids, namely either into an intermediate vector or into a binary vector. Due to sequences homologous to the sequences within the T-DNA, the intermediate vectors may be integrated into the Ti- or Ri-plasmid of the Agrobacterium due to homologous recombination. This also contains the vir-region necessary for the transfer of the T-DNA. Intermediate vectors cannot replicate in Agrobacteria. By means of a helper plasmid the intermediate vector may be transferred to Agrobacterium tumefaciens (conjugation).

Binary vectors may replicate in E.coli as well as in Agrobacteria. They contain a selectable marker gene as well as a linker or polylinker which is framed by the right and the left T-DNA border region. They may be transformed directly into the Agrobacteria (Holsters et al. Mol. Gen. Genet. 163 (1978), 181–187). The Agrobacterium acting as host cell should contain a plasmid carrying a vir-region. The vir-region is necessary for the transfer of the T-DNA into the plant cell. Additional T-DNA may be present. The Agrobacterium transformed in such a way is used for the transformation of plant cells.

The use of T-DNA for the transformation of plant cells was investigated intensely and described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287.

For transferring the DNA into the plant cells, plant explants may suitably be co-cultivated with Agrobacterium tumefaciens or Agrobacterium rhizogenes. From the infected plant material (e.g. pieces of leaves, stem segments, roots, but also protoplasts or suspension-cultivated plant cells) whole plants may then be regenerated in a suitable medium which may contain antibiotics or biozides for the selection of transformed cells. The plants obtained in such a way may then be examined as to whether the introduced DNA is present or not. Other possibilities in order to introduce foreign DNA by using the biolistic method or by transforming protoplasts are known to the skilled person (cf. e.g. Willmitzer, L., 1993 Transgenic plants. In: Biotechnology, A Multi-Volume Comprehensive Treatise (H. J. Rehm, G. Reed, A. Pühler, P. Stadler, editors), Vol. 2, 627–659, VCH Weinheim-New York-Basel-Cambridge).

Whereas the transformation of dicotyledonous plants via Ti-plasmid vector systems by means of Agrobacterium tumefaciens is well established, more recent studies indicate that also monocotyledonous plants may be suitable for the transformation by means of vectors based on Agrobacterium (Chan et al., Plant Mol. Biol. 22 (1993), 491–506; Hiei et al., Plant J. 6 (1994), 271–282).

Alternative Systems for the transformation of monocotyledonous plants are the transformation by means of a biolistic approach, protoplast transformation, the electroporation of partially permeabilized cells, the introduction of DNA by means of glass fibers.

There are various references in the relevant literature dealing specifically with the transformation of maize (cf. e.g. WO95/06128, EP 0 513 849; EP 0 465' 875). In EP 292 435 a method is described by means of which fertile plants may be obtained starting from mucousless, friable granulous maize callus. In this context it was furthermore observed by Shillito et al. (Bio/Technology 7 (1989), 581) that for regenerating fertile plants it is necessary to start from callus-suspension cultures from which a culture of dividing protoplasts can be produced which is capable to regenerate to plants. After an in vitro cultivation period of 7 to 8 months Shillito et al. obtain plants with viable descendants which, however, exhibited abnormalities in morphology and reproductivity.

Prioli and Söndahl (Bio/Technology 7 (1989), 589) have described how to regenerate and to obtain fertile plants from maize protoplasts of the Cateto maize inbreed line Cat 100-1. The authors assume that the regeneration of protoplast to fertile plants depends on a number of various factors such as the genotype, the physiological state of the donor-cell and the cultivation conditions.

Once the introduced DNA has been integrated in the genome of the plant cell, it usually continues to be stable there and also remains within the descendants of the originally transformed cell. It usually contains a selectable marker which confers resistance against biozides or against an antibiotic such as kanamycin, G 418, bleomycin, hygromycin or phosphinotricine etc. to the transformed plant cells. The individually selected marker should therefore allow for a selection of transformed cells against cells lacking the introduced DNA.

The transformed cells grow in the usual way within the plant (see also McCormick et al., Plant Cell Reports 5 (1986), 81–84). The resulting plants can be cultivated in the usual way and cross-bred with plants having the same transformed genetic heritage or another genetic heritage. The resulting hybrid individuals have the corresponding phenotypic properties.

Two or more generations should be grown in order to ensure whether the phenotypic feature is kept stably and whether it is transferred. Furthermore, seeds should be harvested in order to ensure that the corresponding phenotype or other properties will remain.

The examples illustrate the invention.
Abbreviations used

| | |
|---|---|
| bp | base pair |
| GBSS | granule bound starch synthase |
| IPTG | isopropyl β-D-thiogalacto pyranoside |
| SS | starch synthase |
| SSS | soluble starch synthase |

Media and solutions used in the examples:

| | | |
|---|---|---|
| 20 x SSC: | 175.3 g NaCl | |
| | 88.2 g sodium citrate | |
| | ad 1000 ml with ddH$_2$O | |
| | ph 7.0 with 10 N NaOH | |
| YT | 8 g Bacto-Yeast extract | |
| | 5 g Bacto-Tryptone | |
| | 5 g NaCl | |
| | ad 1000 ml with ddH$_2$O | |

Protoplast isolation medium (100 ml)

| | |
|---|---|
| Cellulase Onozuka R S (Meiji Seika, Japan) | 800 mg |
| Pectolyase Y 23 | 40 mg |
| KNO$_3$ | 200 mg |
| KH$_2$PO$_4$ | 136 mg |
| K$_2$HPO$_4$ | 47 mg |
| CaCl$_2$ 2H$_2$O | 147 mg |
| MgSO$_4$ 7H$_2$O | 250 mg |
| Bovine serum albumine (BSA) | 20 mg |
| Glucose | 4000 mg |
| Fructose | 4000 mg |
| Sucrose | 1000 mg |
| pH | 5.8 |
| Osmolarity | 660 mosm. |

Protoplast washing solution 1: like protoplast isolation solution, but without cellulase, pectolyase and BSA.
Transformation buffers:

| | | |
|---|---|---|
| a) | Glucose | 0.5 M |
| | MES | 0.1% |
| | MgCl$_2$ 6H$_2$O | 25 mM |
| | pH | 5.8 |
| | adjust to 600 mosm. | |

| | | |
|---|---|---|
| b) | PEG 6000-solution | |
| | Glucose | 0.5 M |
| | MgCl$_2$ 6H$_2$O | 100 mM |
| | Hepes | 20 mM |
| | pH | 6.5 |

PEG 6000 is added to the buffer described in b) immediately prior to the use of the solution (40% w/v PEG). The solution is filtered with a 0.45 μm sterile filter.
W5 solution

| | |
|---|---|
| CaCl$_2$ | 125 mM |
| NaCl | 150 mM |
| KCl | 5 mM |
| Glucose | 50 mM |

Protoplast culture medium (indicated in mg/l)

| | |
|---|---|
| KNO$_3$ | 3000 |
| (NH$_4$)$_2$SO$_4$ | 500 |
| MgSO$_4$ 7H$_2$O | 350 |
| KH$_2$PO$_4$ | 400 |
| CaCl$_2$ 2H$_2$O | 300 |

Fe-EDTA and trace elements as in the Murashige-Skoog medium (Physiol. Plant, 15 (1962), 473).

| | |
|---|---|
| m-inosite | 100 |
| Thiamine HCl | 1.0 |
| Nicotine acid amide | 0.5 |
| Pyridoxine HCl | 0.5 |
| Glycine | 2.0 |
| Glucuronic acid | 750 |
| Galacturonic acid | 750 |
| Galactose | 500 |
| Maltose | 500 |
| Glucose | 36.000 |
| Fructose | 36.000 |
| Sucrose | 30.000 |
| Asparagine | 500 |
| Glutamine | 100 |
| Proline | 300 |
| Caseinhydrolysate | 500 |
| 2,4 dichlorophenoxy acetic acid (2,4-D) | 0.5 |
| pH | 5.8 |
| Osmolarity | 600mosm. |

In the example the following methods were used:
1. Cloning
   For cloning in *E.coli* the vector pBluescript II SK (Stratagene) was used.
2. Bacterial strains
   For the Bluescript vector and for the pUSP constructs use was made of the *E.coli* strain DH5α (Bethesda Research Laboratories, Gaithersburgh, USA). For in vivo excision the *E.coli* strain XL1-Blue was used.
3. Transformation of maize
   (a) Production of protoplasts of the cell line DSM 6009
   Protoplast isolation
   2–4 days, preferably 3 days after the last change of medium in a protoplast suspension culture the liquid medium is pumped off and the remaining cells are washed in 50 ml protoplast washing solution 1 and sucked dry once more. 10 ml protoplast isolation medium are added to 2 g of harvested cell mass. The resuspended cells and cell aggregates are incubated at 27±2° C. for 4 to 6 hours in the darkness, while shaking it slightly (at 30 to 40 rpm).

Protoplast purification

As soon as the release of at least 1 million protoplasts/ml has taken place (microscopic inspection), the suspension is sifted through a stainless steel or nylon sieve with a mesh size of 200 or 45 $\mu$m. The combination of a 100 $\mu$m and a 60 $\mu$m sieve allows for separating the cell aggregates just as well. The protoplast-containing filtrate is examined microscopically. It usually contains 98–99% protoplasts. The rest are undigested single cells. Protoplast preparations with such a degree of purity are used for transformation experiments without additional gradient centrifugation. The protoplasts are sedimented by means of centrifugation (100 UpM in the swing-out rotor (100×g, 3 minutes)). The supernatant is abandoned and the protoplasts are resuspended in washing solution 1. The centrifugation is repeated and the protoplasts are subsequently resuspended in the transformation buffer.

(b) Protoplast transformation

The protoplasts resuspended in the transformation buffer are filled in 10 ml portions into 50 ml polyallomer tubes at a titer of 0.5–1×10$^6$ protoplasts/ml. The DNA used for transformation is dissolved in Tris-EDTA (TE) buffer solution. 20 $\mu$g plasmid DNA is added to each ml protoplast suspension. A plasmid which provides for resistance to phosphinotricine is used as vector (cf. e.g. EP 0 513 849). After the addition of DNA the protoplast suspension is carefully shaken in order to homogeneously distribute the DNA in the solution. Immediately afterwards 5 ml PEG solution is added in drops. By carefully shaking the tubes the PEG solution is distributed homogeneously. Afterwards further 5 ml of PEG solution are added and the homogenous mixing is repeated. The protoplasts remain in the PEG solution for 20 minutes at ±2° C. Afterwards the protoplasts are sedimented by centrifuging for 3 minutes (100 g; 1000 Upm). The supernatant is abandoned. The protoplasts are washed in 20 ml W5 solution by careful shaking and are again subjected to centrifugation. Then they are resuspended in 20 ml protoplast culture medium, centrifuged anew and again resuspended in culture medium. The titer is adjusted to 6–8×10$^5$ protoplasts and the protoplasts are cultivated in 3 ml portions in Petri dishes (Ø 60 mm, height 15 mm). The Petri dishes are sealed with a parafilm and stored in darkness at 25±2° C.

(c) Protoplast culture

During the first 2–3 weeks after the protoplast isolation and transformation the protoplasts are cultivated without adding fresh medium. As soon as the cells regenerated from the protoplasts have developed into cell aggregates with more than 20 to 50 cells, 1 ml of fresh protoplast culture medium, containing sucrose as an osmotic (90 g/l), is added.

(d) Selection of transformed maize cells and plant regeneration

3–10 days after adding fresh medium the cell aggregates developed from the protoplasts may be plated on Agar media with 100 mg/l L-phosphinothricine. N6-medium with the vitamins of the protoplast culture medium, 90 g/l sucrose and 1.0 mg/l 2,4D is as suitable as an analogous medium such as a medium with the macro- and micro-nutritive salts of the MS medium (Murashige and Skoog (1962), see above).

The calli developed from stably transformed protoplasts may grow further on the selective medium. After 3 to 5 weeks, preferably 4 weeks the transgenic calli may be transferred to fresh selection medium which also contains 100 mg/l L-phosphinothricine which, however, does no longer contain auxine. Within 3 to 5 weeks approximately 50% of the transgenic maize calli which had integrated the L-phosphinothricine-acetyl-transferase gene into their genome, start to differentiate into plants on this medium in the presence of L-phosphinothricine.

(e) Growing of transgenic regenerative plants

The embryogenic transformed maize tissue is cultivated on hormone-free N6-medium (Chu C. C. et al., Sci. Sin. 16 (1975), 659) in the presence of 5×10$^{-4}$ M L-phosphinothricine. On this medium maize embryos, which express the phosphinothricine-acetyl-transferase gene (PAT gene) in a sufficiently strong manner, develop into plants. Non-transformed embryos or such with only a very weak PAT activity die down. As soon as the leaves of the in-vitro plants have reached a length of 4 to 6 mm, they may be transferred into soil. After washing off the Agar residues at the roots the plants are planted into a mixture of clay, sand, vermiculite and potting soil with the ratio 3:1:1:1 and adapted to the soil culture at 90–100% of relative atmospheric humidity during the first 3 days after planting. The growing is carried out in a climate chamber with a 14 hour light period of approximately 25000 lux at the height of the plant at a day/night temperature of 23±1/17±1° C. The adapted plants are cultivated at an 65±5% atmospheric humidity.

4. Radioactive labeling of DNA fragments

The radioactive labeling of DNA fragments was carried out by means of a DNA-Random Primer Labeling Kits by Boehringer (Germany) according to the manufacturer's instructions.

EXAMPLE 1

Identification, isolation and characterization of a cDNA encoding a novel isotype of a starch synthase from *Zea mays*.

In order to identify a cDNA encoding a novel starch synthase from maize the strategy of the functional expression in a suitable *E.coli* mutant was pursued. As a storage carbohydrate, *E.coli* synthesizes on specific nutrient media (complete medium with 1% glucose) a polysaccharide the structure of which resembles that of amylopectin; however, it exhibits a higher degree of branching (7–10% branching points vis-à-vis 4–5%) and usually a higher molecular weight. The higher degree of branching also causes a different iodine staining. Iodine gives a brownish staining to glycogen, a purple staining to amylopectin and a blue staining to amylose.

In *E.coli* three genes are essentially responsible for glycogen synthesis, namely glgA, glgB and glgC which encode glycogen synthase, the branching enzyme and the ADP glucose pyrophosphorylase. This system is analogous to that of the starch biosynthesis in plants. If a plant starch synthase is expressed by wildtype *E.coli* cells, it is difficult or impossible to determine the influence of the enzyme on the properties of the glycogen with the help of the iodine staining since the branching enzyme introduces branch points in the glucans produced by the starch synthase in the same way as into the glucans produced by the glycogen synthase.

Therefore, an *E.coli* strain was produced which allows for a simple screening after the functional expression of a starch synthase by means of iodine staining. For this purpose, the mutant HfrG6MD2 (Schwartz, J. Bacteriol. 92 (1966), 1083–1089) in which all glg genes are deleted, was transformed with the plasmid pACAC. This plasmid contains a DNA fragment encoding the ADP glucose pyrophosphorylase (AGPase) from *E.coli* under the control of the lac Z promoter. The fragment had been isolated from the pEcA-15 vector (see e.g. Müller-Röber (1992), dissertation, FU Berlin) as a DraI/HaeII fragment with the approximate size of 1.7 kb and after filling in its sticky ends it had been cloned into a pACAC184 vector linearized with HindIII. This plasmid mediates the expression of a mutated, deregulated ADP glucose pyrophosphorylase from the *E.coli* strain LCB 618 which accumulates considerable amounts of glycogen due to the mutation of this enzyme (Preiss and Romeo in Advances in Microbial Physiology, Academic Press, London, Vol. 30, 183–238). This ensures the provision of sufficient amounts of ADP glucose, the substrate of starch synthases, and is supposed to ensure the synthesis of linear α-1,4-glucans in *E.coli* HfrG6MD2 which may be stained blue by iodine, when simultaneously functionally expressing starch synthases. Furthermore, the plasmid pACAC, as a derivative of the vector pACYC184 is compatible with plasmids such as the pBluescript SK (−).

This strain was transformed with a cDNA library contained in the pBluescript SK (−) vector and produced from RNA from leaves of Zea mays, line B73. This was produced by initially converting approximately $10^6$ phases of a cDNA library from RNA from leaves of *Zea mays,* line B37, contained in the Uni-ZAPTMXR vector (Stratagene GmbH, Heidelberg), into phagmides by means of in vivo excision. *E.coli* XL1-Blue cells were infected with these phagmids and $3 \times 10^5$ transformants were plated on solid selective (ampicilline-containing) nutrient medium. After growth the cells were washed off and plasmid DNA was prepared therefrom. The transfer of the plasmid DNA into the bacterial cells was carried out according to the method of Hanahan (J. Mol. Biol. 166 (1983), 557–580). Approximately $4 \times 10^5$ transformed *E.coli* cells were spread on Agar culture media having the following composition:

YT medium with:
1.5% Bacto Agar
1% glucose
10 mg/l chloramphenicol
50 mg/l ampicilline
1 mM IPTG
2 mM diaminopimelinic acid After overnight incubation at 37° C. the cells were treated with with iodine vapor. A blue-stained colony was obtained. From this colony, plasmid DNA was isolated and used for repeated transformation. The obtained transformants were spread on replica plates. One of the replica plates was again stained. Blue-staining clones were grown for the preparation of elevated amounts of plasmid DNA.

After examining the size of the cDNA fragment the clone pSSZm was further analyzed.

EXAMPLE 2

Sequence analysis of the cDNA insertion of the plasmid pSSZm

From an *E.coli* clone obtained according to example 1, the plasmid pSSZm was isolated and its cDNA insertion was determined by standard routines using the didesoxynucleotide method (Sanger et al., Proc. Natl. Acad. Sci. USA 74 (1977), 5463–5467). The insertion has a length of 2651 bp and constitutes a partial cDNA. The nucleotide sequence is indicated under Seq ID No. 1. The corresponding amino acid sequence is shown under Seq ID No. 2.

A sequence analysis and a sequence comparison with known sequences showed that the sequence indicated under Seq ID No. 1 is new and comprises a partial coding region which exhibits certain homologies to starch synthases from various organisms. Moreover, the encoded protein constitutes a new isotype of starch synthases which may not be unambiguously grouped among the classes described so far. Within the framework of this application the protein encoded by this cDNA insertion or by hybridizing sequences is designated SSZm. By means of this partial cDNA sequence it is possible for a person skilled in the field of molecular biology without further ado to isolate the full-length clones containing the complete coding region and to determine its sequence. For this purpose, e.g. a leaf-specific cDNA expression library from Zea mays, line B73 (Stratagene GmbH, Heidelberg) is screened for full-length clones by means of hybridization with a 5'-fragment of the cDNA insertion of the plasmid pSSZM (200 bp). Another possibility for obtaining the missing 5'-terminal sequences is to make use of the 5'-Race method (Stratagene cf. manufacturer).

We claim:

1. An isolated nucleic acid molecule comprising a regulatory element operably linked to a part of a nucleic acid sequence in antisense orientation thereto, wherein the nucleic acid sequence is selected from the group consisting of:

(a) a nucleic acid sequence encoding a protein comprising the amino acid sequence of SEQ ID NO: 2;

(b) the nucleic acid sequence of SEQ ID NO: 1; and (c) a nucleic acid sequence that has more than 90% sequence identity to the nucleic acid sequence of (a) or (b);

wherein the part is sufficient to reduce the expression of a soluble starch synthase gene in a plant cell when introduced in antisense orientation with respect to the regulatory element.

2. The nucleic acid molecule according to claim 1, wherein said nucleic acid sequence is selected from the group consisting of:

(a) a nucleic acid sequence encoding a protein comprising the amino acid sequence of SEQ ID NO: 2; and (b) the nucleic acid sequence of SEQ ID NO: 1.

3. The nucleic acid molecule according to claim 2, wherein said nucleic acid molecule comprises the nucleic acid sequence of the coding region of SEQ ID NO: 1.

4. The nucleic acid molecule according to claim 2, wherein said nucleic acid molecule comprises said nucleic acid sequence encoding a protein comprising the amino acid sequence of SEQ ID NO: 2.

5. A vector comprising the nucleic acid molecule according to any one of claims 1, 2, 3 or 4.

6. A host cell transformed with the nucleic acid molecule according to any one of claims 1, 2, 3 or 4, or with a vector comprising said nucleic acid molecule.

7. The host cell according to claim 6, wherein the host cell is a plant cell.

8. A plant comprising the plant cell according to claim 7.

9. The plant according to claim 8, wherein the plant is a starch-storing and/or starch-synthesizing plant.

10. The plant according to claim 9, wherein the plant is a starch-storing plant.

11. The plant according to claim 9, wherein the plant is selected from the group consisting of rye, barley, wheat, rice, maize, pea, cassava and potato.

12. The plant according to claim 9, wherein the plant is a maize plant.

13. A propagation material comprising the plant cell according to claim 7.

14. A propagation material of the plant according to claim 8, wherein said propagation material comprises said plant cell.

\* \* \* \* \*